United States Patent [19]

Behr et al.

[11] Patent Number: 5,093,143
[45] Date of Patent: Mar. 3, 1992

[54] DIETETIC NUTRIENT COMPOSITIONS FOR PATIENTS WITH KIDNEY INSUFFICIENCY

[75] Inventors: Horst Behr, Herford; Friedrich Manz, Dortmund-Bruenninghausen, both of Fed. Rep. of Germany

[73] Assignee: Milchwerke Westfalen eG, Herford, Fed. Rep. of Germany

[21] Appl. No.: 642,893

[22] Filed: Jan. 18, 1991

[30] Foreign Application Priority Data

Jan. 26, 1990 [DE] Fed. Rep. of Germany ....... 4002204

[51] Int. Cl.$^5$ ................................................. A23C 9/20
[52] U.S. Cl. ................................... 426/583; 424/535; 426/657; 426/800; 426/801
[58] Field of Search ............... 426/583, 800, 801, 657, 426/804; 424/535

[56] References Cited

U.S. PATENT DOCUMENTS

| | | | |
|---|---|---|---|
| 3,201,256 | 8/1965 | Clarke | 426/583 |
| 3,896,240 | 7/1975 | Gruette | 426/583 |
| 4,042,576 | 8/1977 | Eustache | 426/583 |
| 4,265,924 | 5/1981 | Buhler | 426/657 |
| 4,400,315 | 8/1983 | Thomas | 426/657 |
| 4,436,658 | 3/1984 | Peyrouset | 426/657 |
| 4,497,836 | 2/1985 | Marquardt | 426/801 |
| 4,740,462 | 4/1988 | Brule | 426/657 |
| 4,748,034 | 5/1988 | de Rham | 426/583 |
| 4,782,138 | 11/1988 | Rialland | 426/657 |
| 4,849,241 | 7/1989 | Al-Mashiki | 426/583 |
| 4,879,131 | 11/1989 | de Rahm | 426/801 |
| 4,897,279 | 1/1990 | Lehmann | 426/583 |
| 4,954,361 | 9/1990 | Girsh | 426/583 |
| 4,970,088 | 11/1990 | Tanaka | 426/583 |
| 4,980,450 | 12/1990 | Brule | 424/535 |

FOREIGN PATENT DOCUMENTS

| | | | |
|---|---|---|---|
| 0311283 | 4/1989 | European Pat. Off. | 426/657 |
| 0355399 | 2/1990 | European Pat. Off. | 426/657 |
| 0371659 | 6/1990 | European Pat. Off. | 426/657 |
| 0390633 | 10/1990 | European Pat. Off. | 426/657 |
| 61-268138 | 11/1986 | Japan | 426/657 |
| 2-117366 | 5/1990 | Japan | 426/583 |
| WO88/08673 | 5/1988 | PCT Int'l Appl. | 426/657 |
| 2188526 | 10/1987 | United Kingdom | 426/657 |

OTHER PUBLICATIONS

21 CFR Part 105, pp. 58–63, 1982.
Webb et al, 1965 Fundamentals of Dairy Chemistry, pp. 80–87, AVI Publishing Co., Inc., Westport, Conn.
Grune Liste 1989 [Green List 1989], Editio Cantor Aulendorf, 1989.

*Primary Examiner*—Carolyn Paden
*Attorney, Agent, or Firm*—Laubscher, Presta & Laubscher

[57] ABSTRACT

Dietetic nutrient compositions suitable for consumption by patients with kidney insufficiency comprise proteins, fats, carbohydrates, and mineral substances in a manner resembling cow's milk as regards the sensory aspects and the processability. The compositions have a high total energy content, are albumin-poor and phosphorus-poor and have a high calcium content. The compositions have good taste properties and are suitable for sustained treatment of patients with chronic kidney insufficiency. The compositions can be processed in the context of numerous lactovegetable recipes.

8 Claims, No Drawings

DIETETIC NUTRIENT COMPOSITIONS FOR PATIENTS WITH KIDNEY INSUFFICIENCY

FIELD OF THE INVENTION

This invention relates to dietetic nutrient compositions particularly suitable for consumption by patients having kidney insufficiency, i.e. irregularly functioning kidneys. The compositions of the invention have reduced albumin and phosphorus contents and comprise protein, fats, carbohydrates and mineral substances.

BACKGROUND OF THE INVENTION

Known dietetic nutrient compositions for patients with kidney insufficiency (Green List, 1989, Alendorf: Edition Cantor, Numbers 12005, 14004) comprise an albumin component in the form of oligopeptides and have a total energy content of about 100-130 kcal/100 ml and a phosphorus content of about 10-13 mg/g protein. An albumin component in the form of oligopeptides is disadvantageous in that, owing to the destruction of the structure of the protein due to the procurement of the oligopeptide, there is no longer any meaningful possibility for kitchen processability. Additionally, the sensory qualities of the compositions differ considerably from those of cow's milk. For example, the very bad taste of oligopeptides significantly impairs patient acceptance, particularly when sustained use is required. Further, the total energy content of the compositions appears to be relatively small while the phosphate content is at the upper limit of desirability.

WO 88/02219 discloses a phosphorous-reducing milk having a lower phosphate content which is within the upper limit of desirability for patients with kidney insufficiency. The albumin component of the milk is based on casein proteins which are obtained by precipitation with lactic acid from skim milk. Phosphoric acid is precipitated by means of calcium from the remaining whey, after which the casein is readded. However, phosphorus which, at the moment of precipitation, is still trapped in casein proteins remains in the product whereby the desirable low phosphorus values cannot be attained using these casein proteins. Additionally, lactic acid treatment can, at least in terms of tendencies, lead to structural changes that could make kitchen processing of the milk more difficult. Further, the overwhelming portion of the protein in the milk comes from casein and therefore disadvantageously has a relatively small content of essential amino acids that otherwise would have a very high valence for the patient. Finally, the process involved in obtaining casein proteins by means of precipitation and their reconstitution results in a product which generally can be sold commercially only in the liquid form.

From the Green List 1989, Aulendorf, Edition Cantor, No. 01005, an albumin-poor beverage produced from whey components is known. The beverage is designed for amino acid metabolism disorders that lead to the formation of toxic metabolism products in the patient. The beverage product has an increased phosphorous content of more than 38 mg/g protein and therefore is prohibited for administration to patients with kidney insufficiency. Additionally, the total energy content of the beverage is unacceptably low for patients with kidney insufficiency.

Thus, a need exists for a dietetic nutrient which is suitable for consumption by patients with kidney insufficiency and which overcomes the disadvantages of these known compositions.

SUMMARY OF THE INVENTION

Accordingly, a purpose of the present invention is to provide dietetic nutrient compositions suitable for consumption by patients with kidney insufficiency which, even in cases of sustained use, provide a low level of phosphate and a calorically adequate supply to the patient and which supply the patient with albumin having a large share of essential amino acids. Additional objects of the present invention are to provide a reduced albumin content in the compositions and to provide a tasty product which can be well processed through kitchen technology.

These and additional objects and purposes are achieved by the dietetic nutrient compositions of the invention. The compositions comprise native whey protein, fats, carbohydrates and mineral substances. The compositions have a total energy content of 50-500 kcal/100 ml, 1-10% of which is provided by protein components, and a phosphorus content of less than 10 mg/g protein. Additionally, the albumin component of the compositions of the invention is formed from native protein obtained essentially from whey.

The high acceptance rate of the present dietetic nutrient compositions in patients results from the fact that they are similar to milk in sensory and technical kitchen terms. That is, in taste, odor, and appearance, the present compositions resemble milk and can be processed like milk. The compositions can be drunk hot or cold and can also be processed into additional, numerous recipes that will retain their good taste, especially on a lactovegetable basis. While complying with the basic dietetic principles required for dietary treatment of kidney insufficiency, the present nutrient compositions have a high energy content and can definitely be described as calorie-rich, as indicated by the energy content of 50-500 kcal/100 ml. In comparison, cow's milk generally has an energy content on the order of 66 kcal/100 ml and is already described as an energy-rich beverage. An additional important feature is that the dietetic nutrient compositions according to the invention are albumin-poor in terms of the dietetic regulations because only 1-10% of the total energy content is formed by the protein component. Further, in view of dietetic regulations, it is also important that the phosphorus content is less than 10 mg/g protein. In spite of their similarity to milk, the nutrient compositions of the invention are phosphorus-poor. Furthermore, the protein component essentially is formed from whey protein whereby, in this connection, the word "protein" is to be understood as meaning native protein. This phenomenon essentially helps in replicating cow's milk in both cooking and sensory terms. The use of whey proteins also offers the great advantage that the compositions provide an optimum portion of essential amino acids which, in spite of the requirement for albumin poverty, may be at the level of a patient's daily requirement without increasing urea volume into a critical range.

In additional embodiments, the compositions comprise up to 300 mg calcium 100 ml. The product is thus calcium-rich and therefore further resembles milk and dairy products. With the product being so constituted, one can partially eliminate treatment with calcium tablets that is often required in customary kidney insufficiency diets in a continuing fashion and which, in the long run, has a very disturbing effect in terms of taste.

The heavy dose of calcium moreover offers a patient with kidney insufficiency the advantage that calcium absorption from the intestines is essentially normalized and phosphorus absorption from the intestines is simultaneously reduced by the formation of insoluble calcium phosphate in the intestines.

In a further embodiment, fat content of the nutrient compositions is preferably formed from vegetable fats, which is advantageous from a nutrition-physiology aspect.

The invention is described below in greater detail.

DETAILED DESCRIPTION

The dietetic nutrient compositions according to the invention comprise proteins, fats, carbohydrates and mineral substances. The compositions comprise these substances in a manner resembling cow's milk in sensory and cooking terms, that is, the compositions taste and odor resemble that of cow's milk, the compositions look like cow's milk, and, in physical and chemical terms, the compositions behave like cow's milk, in cooking technology. The compositions can be drunk either cold or hot, equally, or can be processed in diverse, pleasantly tasting recipes.

The aforementioned components are so assembled that the nutrient compositions energy content is 50-500 kcal/100ml. The total energy content thus is high. The nutrient compositions are calorie-rich and thus prevent the caloric supply shortfall which is observed in many patients who are given this kind of diet. In comparison, cow's milk itself has an energy content of 66 kcal/100 ml and is already described as an energy-rich beverage. Fruit juices, vegetable juices, and the like have an energy content of less than 50 kcal/100 ml. For the nutrient compositions according to the invention, an energy content of 100-200 kcal/100 ml is particularly practical.

One feature of the present compositions that is essential in terms of the dietetic requirements for kidney insufficiency is that, looking at the above-mentioned total energy content, the energy content provided by the protein component of the nutrient compositions is only 1-10% of the total energy content. The higher percentage ranges here are meaningful for dialysis patients wherein, due to the loss of proteins and albumin building blocks in the course of dialysis, the albumin content in the nutrient composition may be somewhat higher than for patients who do not require dialysis. A particularly practical percentage range is between 3 and 7%. In the lower range, the nutrient composition can at any rate still be described as extremely, albumin-poor. In the upper range likewise the nutrient composition can still be said to be albumin-poor although it allows a higher albumin content which is permissible especially in individual groups of patients.

Utmost care should be taken to make sure that the generally relatively small albumin component if at all possible is supplied in the form of biologically high-grade albumin. It is preferred to form the protein part essentially from milk albumin, and more preferably from whey. That, for example, can be done by subjecting the whey, whose protein content as a rule is 0.6-0.8%, to ultrafiltration. As a result, the constituents of the whey are separated according to their molecular weight. Low-molecular substances, such as water, lactose, and salts, can pass through the membranes while the high-molecular whey proteins are retained. One can adjust the process to obtain differing concentration degrees. The albumin content of the whey protein product used for the nutrient compositions according to the invention is between 40 and 80%. In these whey proteins, the share of essential amino acids, in other words those albumin building blocks that the human body itself cannot form, is particularly high.

In the nutrient compositions' mineral substances, special care is taken so that the phosphorus content is low. It is, at most, 15 mg/g of protein, preferably less than 10 mg/g protein, and in a typical practical case it is 5 mg/g protein. A low phosphorus supply is an essential goal in the sustained dietetic treatment of patients with kidney insufficiency.

As a further preferred feature, care should be taken in the mineral substances to ensure that there is a high calcium content. The calcium content can be as high as 350 mg/100 ml and should not fall below a lower limit of 25 mg/100 ml. The calcium content of milk is 120 mg/100 ml. In a preferred composition, the calcium content is close to that of milk. Milk and dairy products represent the most important calcium source in nutrition. They are generally considered to be calcium-rich essential foods. A high calcium content justifies the nutrition-physiology expectations of consumers in general and of kidney patients, in particular, in a milk product. Moreover, patients with kidney insufficiency depend on a high calcium supply from the intestines due to a reduction in calcium absorption which is specifically connected with this illness. Additionally, a high calcium supply reduces phosphorus absorption from the intestines in a desirable fashion through the formation of insoluble calcium phosphate in the intestines.

With a view to the low protein content, the relatively high total energy content of the nutrient compositions must be adjusted via the fat and carbohydrate components. Although animal fats are basically suitable, the preferred use of vegetable fats is particularly practical from the nutrition-physiology aspect. In the case of the carbohydrates, dextrins are preferred from the nutrition-physiology aspect.

The dietetic nutrient compositions according to the invention are best sold commercially in powder form with reference to the usual way in which the components are produced. The finished preparation, which is to resemble milk, can be achieved by adding boiled water and stirring.

EXAMPLE

A typical example of a dietetic nutrient composition according to the invention, is set forth in the following analysis in the table. In the first column, the components are set forth per 100 g in powder form; in the second column the components are set forth per 100 ml of the dietetic nutrient composition. Column 3 in the Table shows the composition of the 100 ml of drinking whole milk, for comparison.

TABLE

|  |  | 100 g powder of the dietetic nutrient | 100 ml of the dietetic nutrient composition | 100 ml of whole milk |
|---|---|---|---|---|
| Protein | g | 4.7 | 1.0 | 3.3 |
| Alanine | mg |  | 52 | 120 |
| Arginine | mg |  | 28 | 120 |
| Asparginic acid | mg |  | 101 | 280 |
| Cystine | mg |  | 17 | 26 |
| Glutamic acid | mg |  | 178 | 750 |
| Glycine | mg |  | 20 | 80 |

TABLE-continued

|  | | 100 g powder of the dietetic nutrient | 100 ml of the dietetic nutrient composition | 100 ml of whole milk |
| --- | --- | --- | --- | --- |
| Histidine | mg |  | 19 | 89 |
| Isoleucine | mg |  | 66 | 210 |
| Leucine | mg |  | 107 | 350 |
| Lysine | mg |  | 90 | 260 |
| Methionine | mg |  | 22 | 84 |
| Phenylalanine | mg |  | 34 | 170 |
| Proline | mg |  | 52 | 350 |
| Serine | mg |  | 48 | 190 |
| Threonine | mg |  | 70 | 150 |
| Tryptophan | mg |  | 15 | 46 |
| Tyrosine | mg |  | 30 | 170 |
| Valine | mg |  | 63 | 230 |
| Fat | g | 18.7 | 4.0 | 3.5 |
| Carbohydrates | g | 70.2 | 15.0 | 4.6 |
| Glucose | g | 0.4 | 0.1 |  |
| Lactose | g | 4.7 | 1.0 | 4.6 |
| Maltose | g | 2.3 | 0.5 |  |
| Dextrines | g | 62.9 | 13.4 |  |
| Mineral Substances | mg | 1100 | 230 |  |
| Sodium | mg | 96 | 20 | 50 |
| Potassium | mg | 30 | 6 | 155 |
| Chlorine | mg | 20 | 4 | 100 |
| Calcium | mg | 565 | 120 | 120 |
| Magnesium | mg | 9 | 2 | 12 |
| Phosphorus | mg | 23 | 5 | 90 |
| Energy | kJ | 1984 | 423 | 279 |
| Osmolarity |  |  | 170 | 250 mosmol/l |

The table shows, looking at the proteins, the large proportion of so-called essential amino acids, in other words, albumin building blocks that are particularly valuable in biological terms, in which connection reference must also be made to the portions of the amino acids contained in the protein, that is isoleucine, leucine, lysine, methionine, phenylalanine, threonine, tryptophan, and valine.

The osmolarity set forth in the Table characterizes the number of dissolved particles in the liquid.

The preceding example is set forth to illustrate the present invention. Additional embodiments of the compositions of the present invention within the scope of the claims will be apparent to those skilled in the art.

What is claimed is:

1. An albumin-containing and phosphorus-containing dietetic nutrient composition which is similar to cow's milk in sensory and cooking properties, comprising native whey protein, fats, carbohydrates and mineral substances, the albumin included in said composition being formed from native protein essentially obtained from whey, said composition having a total energy content of 50–500 kcal/100 ml, 1–10% of said total energy content being provided by protein components of said composition, and a phosphorus content of less than 10 mg/g protein.

2. A dietetic nutrient composition as defined by claim 1, comprising up to 300 mg calcium/100 ml.

3. A dietetic nutrient composition as defined by claim 1, having a total energy content of 100–200 kcal/100 ml.

4. A dietetic nutrient composition as defined by claim 1, wherein 3–7% of the total energy content is provided by the protein components of said composition.

5. A dietetic nutrient composition as defined by claim 1, wherein the fats consist essentially of vegetable fats.

6. A dietetic nutrient composition as defined by claim 1, wherein the carbohydrates consist essentially of dextrins.

7. A dietetic nutrient composition as defined by claim 1, said composition being in powder form.

8. A dietetic nutrient composition as defined by claim 1, further comprising water and being in liquid form.

* * * * *